United States Patent [19]

Chou et al.

[11] Patent Number: 5,616,713
[45] Date of Patent: Apr. 1, 1997

[54] PROCESS OF PREPARING 2-HYDROXYMETHYL-3,5-DIMETHYL-4-METHOXYPYRIDINE

[75] Inventors: Shan-Yen Chou, Taipei; Tsai-Mien Huang, Changhua; Shyh-Fong Chen; Hao Ku, both of Taipei, all of Taiwan

[73] Assignee: Development Center for Biotechnology, Taipei, Taiwan

[21] Appl. No.: 681,123

[22] Filed: Jul. 22, 1996

[51] Int. Cl.$^6$ .................................. C07D 213/12
[52] U.S. Cl. .................. 546/250; 546/298; 546/301; 549/420; 568/628; 568/687; 568/909.5
[58] Field of Search .................... 546/250, 298, 546/301; 549/420; 568/628, 687, 909.5

[56] References Cited

U.S. PATENT DOCUMENTS 5,066,810  11/1991  Baumann .................. 546/300

OTHER PUBLICATIONS

Xue, T. et al, Huaxue Xuebao, 1986, 44(11), pp. 1129–1133.
Bobosik, V., et al, Monatsh. Chem. 1995, 126(6/7), pp. 747–752.
Kontoghiorghes, G.J. et al, Inorg. Chim. Acta, 1987, 136, pp. L11–L12.

Primary Examiner—C. Warren Ivy
Assistant Examiner—Garth M. Dahlen
Attorney, Agent, or Firm—Fish & Richardson P.C.

[57] ABSTRACT

A process of preparing 2-hydroxymethyl-3,5-dimethyl-4-methoxypyridine including the steps of acylating 2-methyl-1-penten-1-alkoxy-3-one to obtain 2-alkoxycarbonyl-3,5-dimethyl-4-pyrone; ammonolyzing 2-alkoxycarbonyl-3,5-dimethyl-4-pyrone to obtain 2-alkoxycarbonyl-3,5-dimethyl-4(1H)-pyridone; halogenating 2-alkoxycarbonyl-3,5-dimethyl-4(1H)-pyridone to obtain 2-alkoxycarbonyl-4-halo-3,5-dimethylpyridine; methoxylating 2-alkoxycarbonyl-4-halo-3,5-dimethylpyridine to obtain 2-methoxycarbonyl-3,5-dimethyl-4-methoxypyridine; and reducing 2-methoxycarbonyl-3,5-dimethyl-4-methoxypyridine to obtain 2-hydroxymethyl-3,5-dimethyl-4-methoxypyridine.

20 Claims, No Drawings

PROCESS OF PREPARING 2-HYDROXYMETHYL-3,5-DIMETHYL-4-METHOXYPYRIDINE

BACKGROUND OF THE INVENTION

Omeprazole (trade name Prilosec), a specific inhibitor of the gastric proton pump $(H^+ + K^+)$-ATPase, can be prepared by coupling 2-chloromethyl-3,5-dimethyl-4-methoxypyridine and 5-methoxy-2-mercaptobenzimidazole, followed by oxidation. 2-chloromethyl-3,5-dimethyl-4-methoxypyridine, in turn, is readily obtainable by chlorination of 2-hydroxymethyl-3,5-dimethyl-4-methoxypyridine (i.e., compound 9 shown in Scheme A below).

Conventional methods of preparing compound 9 involve using either N-oxide or nitropyridine as an intermediate. E.g., see U.S. Pat. No. 4,255,431 (1981) and European Patent Application 369,208 (1990). Both N-oxide and nitropyridine have been reported to be carcinogenic.

SUMMARY OF THE INVENTION

The present invention features a process of preparing 2-hydroxymethyl-3,5-dimethyl-4-methoxypyridine, including the following steps:

(1) acylating 2-methyl-1-penten-1-alkoxy-3-one to obtain 2-alkoxycarbonyl-3,5-dimethyl-4-pyrone (the alkoxy group of 2-methyl-1-penten-1-alkoxy-3-one can contain one or more carbons, e.g., $C_1$–$C_8$ or $C_1$–$C_{12}$);

(2) ammonolyzing 2-alkoxycarbonyl-3,5-dimethyl-4-pyrone to obtain 2-alkoxycarbonyl-3,5-dimethyl-4(1H)-pyridone;

(3) halogenating 2-alkoxycarbonyl-3,5-dimethyl-4(1H)-pyridone to obtain 2-alkoxycarbonyl-4-halo-3,5-dimethylpyridine;

(4) methoxylating 2-alkoxycarbonyl-4-halo-3,5-dimethylpyridine to obtain 2-methoxycarbonyl-3,5-dimethyl-4-methoxypyridine (e.g., using sodium methoxide in refluxing methanol); and (5) reducing 2-methoxycarbonyl-3,5-dimethyl-4-methoxypyridine to obtain 2-hydroxymethyl-3,5-dimethyl-4-methoxypyridine (e.g., using a reducing agent such as $LiAlH_4$, $NaBH_4$, $NaBH_4$/Lewis acid, $NaBH_4$/tetrahydrofuran ("THF"), $NaBH_4$/tetrahydrofuran/MeOH, $AlH_3$, and diisobutylaluminum hydride).

More specifically, the acylating step can be performed by contacting 2-methyl-1-penten-1-alkoxy-3-one with a dialkyloxylate (e.g., diethyloxylate) to obtain 2-alkoxycarbonyl-3,5-dimethyl-4-pyrone. Note that the two alkyl groups of dialkyloxylate can be either the same or different and each may contain one or more carbons, e.g., $C_1$–$C_8$.

The ammonolyzing step, on the other hand, can be effected by contacting 2-alkoxycarbonyl-3,5-dimethyl-4-pyrone with benzylamine or substituted benzylamine (e.g., a methyl substituent on the benzene ring) to obtain N-benzyl-2-alkoxycarbonyl-3,5-dimethyl-4-pyridone or N-substituted benzyl-2-alkoxycarbonyl-3,5-dimethyl-4-pyridone and then converting N-benzyl-2-alkoxycarbonyl-3,5-dimethyl-4-pyridone or N-substituted benzyl-2-alkoxycarbonyl-3,5-dimethyl-4-pyridone to 2-alkoxycarbonyl-3,5-dimethyl-4(1H)-pyridone wither by hydrogenation (e.g., $H_2$/Pd—C) or other suitable reducing reagents.

As for the halogenating step, a halogenating agent, such as a chlorinating agent (e.g., $POCl_3$, $POCl_5$, and $SOCl_2$; used either singly or in combination), is used to react with 2-alkoxycarbonyl-3,5-dimethyl-4(1H)-pyridone to obtain 2-alkoxycarbonyl-4-halo-3,5-dimethylpyridine.

Other features or advantages of the present invention will be apparent from the following detailed description and also from the appending claims.

DETAILED DESCRIPTION OF THE INVENTION

Without further elaboration, it is believed that one skilled in the art can, based on the description herein, utilize the present invention to its fullest extent. The following specific examples are, therefore, to be construed as merely representative, and not limitative of the remainder of the disclosure in any way whatsoever. All publications cited in this disclosure are incorporated by reference.

Scheme A below is illustrative of the process of the invention:

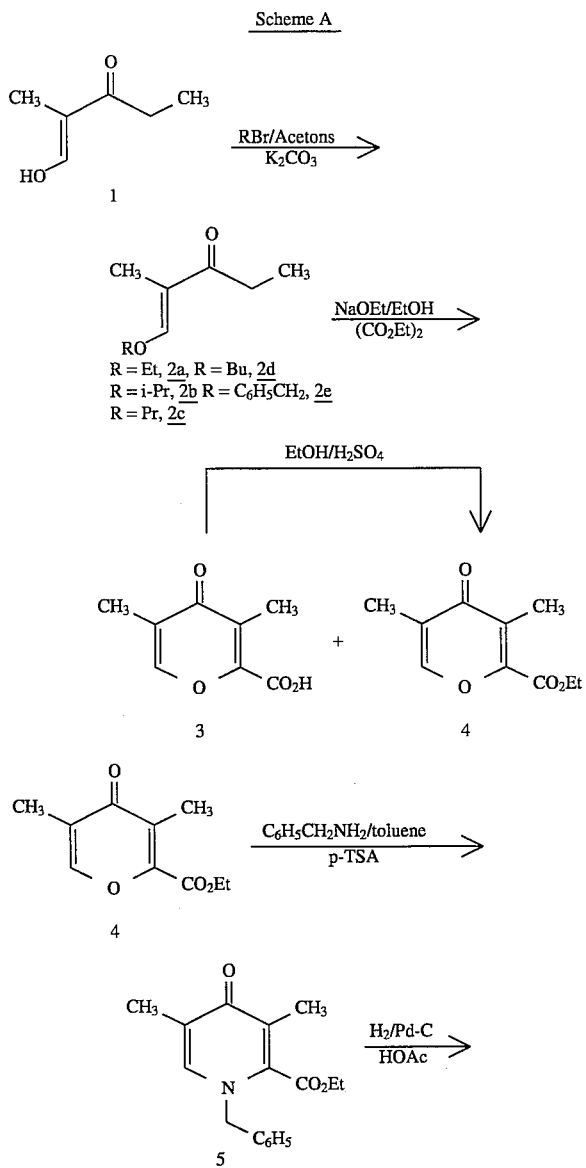

-continued
Scheme A

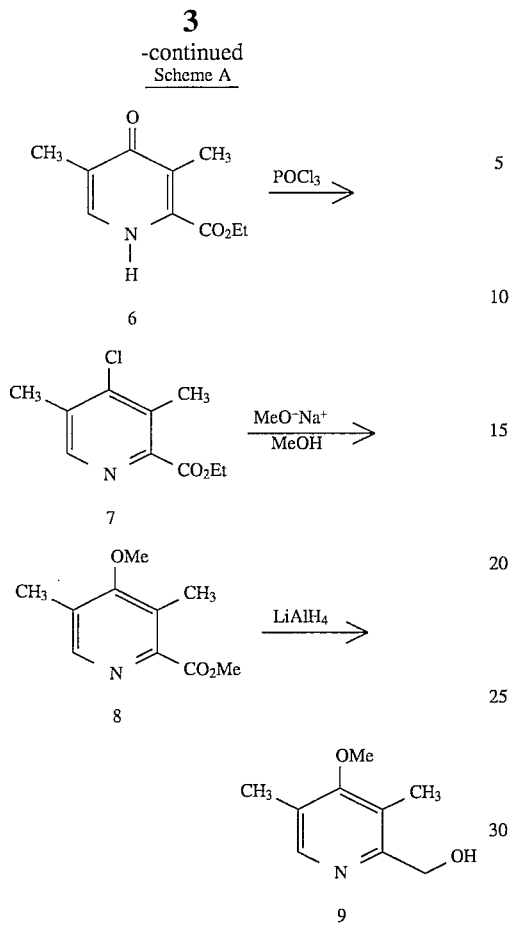

According to Scheme A, O-alkylated product, 2-methyl-1-penten-1-alkoxy-3-one (one of compounds 2a–2e) is prepared by alkylation of 2-methyl-1-penten-3-one-1-ol 1 with alkyl bromide in refluxing acetone. One of compounds 2a–2e is then subjected to acylation followed by concomitant ring-closure using diethyloxalate, producing a mixture of compounds 3 and 4. Compound 3 is a saponification product of compound 4 formed by the residual water present in commercial ethanol (0.2% max). Compound 2a is a reactant which can be most efficiently converted to compound 4. Compound 3 can be converted to compound 4 by esterification. Ammonolyzing of compound 4 with benzylamine in refluxing toluene lead to pyridone derivative 5. Hydrogenation of compound 5 in acetic acid under pressure gives compound 6, which, upon chlorination with phosphoryl chloride, affords compound 7. Methoxylation with concomitant alcoholysis of compound 7 in refluxing methanol in the presence of sodium methoxide yields compound 8, which can be converted to compound 9 by LiAlH$_4$ reduction.

Examples of the process of Scheme A are described in detail below:

Preparation of 2-methyl-1-penten-1-alkoxy-3-one 2a–2e

To a solution of 2-methyl-1-penten-3-one-1-ol 1 (76 g, 0.67 mol) in acetone (1.5 liter) was added ethyl bromide (209 g, 1.92 mol) and anhydrous potassium carbonate (115 g, 0.83 mol). The mixture was refluxed for 34 hr. After the solvent had been evaporated, the residue was treated with water and extracted twice with ether. The ether extract was wished with dilute potassium carbonate and water and dried over anhydrous magnesium sulfate. Evaporation of the ether under reduced pressure followed by vacuum distillation gave 2a (80.3 g, 84% yield) as a yellow oil. $^1$H-NMR (CDCl$_3$) δ 7.33 (s, 1H), 4.08 (q, J=7.2 Hz, 2H), 2.56 (q, J=7.4 Hz, 2H), 1.73 (s, 3H), 1.36 (t, J=7.2 Hz, 3H), 1.13 (t, J=7.4 Hz, 3H). Anal. Calcd for C$_8$H$_{14}$O$_2$: C, 67.5; H, 9.92. Found: C, 67.25; H, 9.87.

In a manner similar to the preparation of 2a, 2-methyl-1-penten-1-alkoxy-3-one 2b–2e was prepared from 2-methyl-1-penten-3-one-1-ol and the corresponding alkyl bromide with an 80–85% yield. 2b, $^1$H-NMR (CDCl$_3$) δ 7 39 (s, 1H), 4.20 (M, 1H), 2.55 (q, J=7.2 Hz, 2H), 1.72 (s, 3H), 1.35 (s, 3H), 1.32 (s, 3H), 1.11 (t, J=7.2 Hz, 3H). Ms(13eV) m/z(%): 156.0(M$^+$, 30) 127.0(32) , 101.9(70) , 85.0(100). 2c, $^1$H-NMR (CDCl$_3$) δ 7.33 (s, 1H), 3.98 (t, J=7.0 Hz, 2H), 2.54 (q, J=7.0 Hz, 2H), 1.73 (s, 3H), 1.10 (t, J=7.0 Hz, 3H), 0.99 (t, J=7.0 Hz, 3H). Ms(13eV) 156.0(M$^+$, 100) 127.0(40), 85.0(50). 2d, $^1$H-NMR (CDCl$_3$) δ 7.32 (s, 1H), 4.02 (t, J=7.0 Hz, 2H), 2.53 (q, J=7.0 Hz, 2H), 1.72 (s, 3H), 1.40 (M, 2H), 1.10 (t, J=7.0 Hz, 3H), 0.92 (t, J=7.0 Hz, 3H). Ms(13eV) 170.0 (M$^+$25), 141.1(50), 85.0(100). 2e, $^1$H-NMR (CDCl$_3$) δ 7.40 (M, 5H), 7.32 (s, 1H), 5.06(S, 2H), 2.51 (q, J=7.2 Hz, 2H), 1.77 (s, 3H), 1.09 (t, J=7.2 Hz, 3H). Ms(13eV) 2.04(M$^+$, 10), 175.1(10), 91.0(100).

Preparation of 2-carboxylic acid-3,5-dimethyl-4-pyrone 3 and 2-ethoxycarbonyl-3,5-dimethyl-4-pyrone 4

To a refluxing solution of ethanolic sodium ethoxide solution (50 ml, 0.626M) was added a mixture of compound 2a (4.05 g, 0.028 mol) and diethyl oxalate (4.1 g, 0.028 mol) over 0.5 hr. After another 0.5 h the solvent was evaporated and the residue was poured into ice-water. The mixture was extracted with dichloromethane (100 ml×2) and washed with water. The organic layer was dried and removal of the solvent gave crude products, which was recrystallized from n-hexane to give 4 as a white powder (2.2 g, 40% yield) m.p. 81°–83° C. $^1$H-NMR (CDCl$_3$) δ 7.73 (s, 1H), 4.42 (q, J=7.2 Hz, 2H), 2.31 (s, 3H), 1.96 (s, 3H), 1.42 (t, J=7.2 Hz, 3H). Ms (13eV) m/z (%): 196.1 (M$^+$, 45), 167.1 (100). Anal. Calcd for C$_{10}$H$_{12}$O$_4$: C, 61.22; H, 6.16. Found: C, 61.18; H, 6.12 .

The aqueous solution and washings were combined and acidified with conc. HCl at 0° C. The resulting precipitate was filtered and dried in vacuo to give 3 as a white powder (0.94 g, 20% yield) mp 185°–187° C. $^1$H-NMR (DMSO-d6) 8.19 (s, 1H), 2.15 (s, 3H), 1.83 (s, 3H). Ms (13eV) m/z (%): 168.0 (M$^+$, 100), 124.1 (20), 95.0 (20). Anal Calcd for C$_8$H$_8$O$_4$: C, 57.15; H, 4.80. Found: C, 57.10; H, 4.75.

Esterification of 2-carboxylic acid-3,5-dimethyl-4-pyrone 3 to 2-ethoxycarbonyl-3,5-dimethyl-4-pyrone 4

To a solution of compound 3 (3 g, 17.7 mmol) in abs. Ethanol (30 ml) was added sulfuric acid (0.5 g). The mixture was refluxed for 5 hr and then the solvent was evaporated. The residue was partitioned between chloroform and 10% potassium carbonate aqueous solution. The separated chloroform layer was washed with water, dried and evaporated to give compound 4 (3.2 g, 92% yield).

In a similar manner, 2-ethoxycarbonyl-3,5-dimethyl-4-pyrone4 was prepared with an overall yield of 30–35% from 2-methyl-1-penten-1-alkoxy-3-one 2b–2e, in which the alkoxy group is isoproxy, proxy, butoxy, and benzyloxy, respectively.

Preparation of N-benzyl-2-ethoxycarbonyl-3,5-dimethyl-4-pyridone 5

A solution of compound 4 (5.0 g, 25.5 mmol), benzylamine (2.92 g, 27.3 mmol) and p-toluenesulfonic acid monohydrate (0.25 g) in toluene (48 ml) was azeotropically refluxed for 9 hr. The resulting solution was washed with 10% $K_2CO_3$, dried and evaporated to give compound 5 (5.1 g, 70% yield) as a yellow oil. $^1$H-NMR (CDCl$_3$) δ 7.10–7.40 (m, 5H), 4.98(5, 2H), 4.17 (q, J=7.1 Hz, 2H), 2.02 (s, 3H), 2.00 (s, 3H), 1.20 (t, J=7.1 Hz, 3H). Ms (13eV) m/z (%): 285.1($M^+$, 60), 271.1(100), 256.0(55), 212.0(20), 180.0(25).

Preparation of 2-Ethoxycarbonyl-3,5-dimethyl-4(1H)-pyridone 6

To a solution of pyridone 5 (5.1 g, 17.89 mmol) in acetic acid (100 ml) was added 10% Pd—C (0.2 g), and the reaction mixture was hydrogenated (55 Psi) at room temperature overnight. The mixture was then filtered through Celite and the filtrate was evaporated. The residue was thoroughly washed with 10% potassium carbonate, water and dried in vacuo to give compound 6 as a white powder (3.3 g, 95% yield) m.p. 124°–126° C. $^1$H-NMR (DMSO-d6) δ 7.52 (brs, 1H), 4.45 (q, J=7.2 Hz, 2H), 2.40 (s, 3H), 2.07 (s, 3H), 1.42(t, J=7.2 Hz, 3H). Ms(13eV)m/z(%): 195.0($M^+$, 100), 165.9(40), 148.9(50), 122.9(80), 121.0(100). Anal. Calcd for $C_{10}H_{13}NO_3$: C, 61.53; H, 6.71; N, 7.18. Found: C, 61.48; H, 6.63; N, 7.09.

Preparation of 2-ethoxcarbonyl-4-chloro-3,5-dimethylpyridine 7

A mixture of pyridone 6 (6.3 g, 32.3 mmol) and phosphoryl chloride (21.8 g, 0.14 mol) was heated at 120° C. for 1 hr. and concentrate in vacuo. The residual oil was cooled and poured into ice water (100 ml) and it was extracted with dichloromethane (50 ml×3). The combined extracts was washed successively with water, saturated sodium bicarbonate aqueous solution, and brine, and then dried. Removal of the solvent in vacuo gave a residue, which was filtered through a short pad of silica gel using 1:5 ethylacetate/hexane and evaporated gave compound 7 (6.1 g, 88% yield) as a yellow oil. $^1$H-NMR (CDCl$_3$) δ 8.36 (s, 1H), 4.45 (q, J=7.0 Hz, 2H), 2.58 (s, 3H), 2.41 (s, 3H), 1.43 ( t, J=7.0 Hz, 3H). Ms(13eV)m/z(%): 214.1($M^+$+1, 100), 183.0(20), 168.0(20), 141.0(65).

Preparation of 2-methoxycarbonyl-3,5-dimethyl-4-methoxypyridine 8

A solution of compound 7 (3.4 g, 15.92 mmol) in methanolic sodium methoxide solution (28 ml, 1.86M, 52.08 mmol) was heated under reflux for 5 hr. After the solvent was evaporated, water was added and it was extracted with dichloromethane. The organic layer was dried and evaporated to give compound 8 (2.5 g, 80% yield) as an oil. $^1$H-NMR δ 8.35 (s, 1H), 3.96 (s, 3H), 3.79 (s, 3H), 2.49 (s, 3H), 2.32 (s, 3H). Ms(13eV) m/z(%): 196.1($M^+$+1, 100), 163.0(20), 137.1(40), 107.1(20).

Preparation of 2-hydroxymethyl-3,5-dimethyl-4-methoxypyridine 9

Lithium aluminum hydride (0.94 g, 25.4 mmol) was dissolved in 100 ml of absolute THF and added in a dropwise manner to a stirred solution of compound 8 (2.5 g, 12.82 mmol) in 20 ml of THF at 0° C. The mixture was stirred at 0° C. for 2 hr. Excess LiAlH$_4$ was then destroyed with ethyl acetate. The combined organic phases were dried, filtered, and evaporated in vacuo to give compound 9 (1.1 g, 50% yield). It gave same analytic data as those of an authentic sample.

OTHER EMBODIMENTS

From the above description, one skilled in the art can easily ascertain the essential characteristics of the present invention, and, without departing from the spirit and scope thereof, can make various changes and modifications of the invention to adapt it to various usages and conditions. For example, a process similar to that described above can be used to preapre analogs of 2-hydroxymethyl-3,5-dimethyl-4-methoxypyridine, such as 2-hydroxymethyl-3,5-dimethyl-4-ethoxypyridine. Thus, other embodiments are also within the claims.

What is claimed is:

1. A process of preparing 2-hydroxymethyl-3,5-dimethyl-4-methoxypyridine, which process comprises the following steps:

acylating 2-methyl-1-penten-1-alkoxy-3-one to obtain 2-alkoxycarbonyl-3,5-dimethyl-4-pyrone;

ammonolyzing said 2-alkoxycarbonyl-3,5-dimethyl-4-pyrone to obtain 2-alkoxycarbonyl-3,5-dimethyl-4(1H)-pyridone;

halogenating said 2-alkoxycarbonyl-3,5-dimethyl-4(1H)-pyridone to obtain 2-alkoxycarbonyl-4-halo-3,5- dimethylpyridine;

methoxylating said 2-alkoxycarbonyl-4-halo-3,5-dimethylpyridine to obtain 2-methoxycarbonyl-3,5-dimethyl-4methoxypyridine; and reducing said 2-methoxycarbonyl-3,5-dimethyl-4-methoxypyridine to obtain 2-hydroxymethyl-3,5-dimethyl-4-methoxypyridine.

2. The process of claim 1, wherein said ammonolyzing step comprises contacting said 2-alkoxycarbonyl-3,5-dimethyl-4-pyrone with benzylamine or substituted benzylamine to obtain N-benzyl-2-alkoxycarbonyl-3,5-dimethyl-4-pyridone or N-substituted benzyl-2-alkoxycarbonyl-3,5-dimethyl-4-pyridone, and converting said N-benzyl-2-alkoxycarbonyl-3,5-dimethyl-4-pyridone or said N-substituted benzyl-2-alkoxycarbonyl-3,5-dimethyl-4-pyridone to said 2-alkoxycarbonyl-3,5-dimethyl-4(1H)-pyridone.

3. The process of claim 2, wherein said halogenating step comprises contacting said 2-alkoxycarbonyl-3,5-dimethyl-4(1H)-pyridone with a chlorinating agent to obtain said 2-alkoxycarbonyl-4-halo-3,5-dimethylpyridine.

4. The process of claim 3, wherein said chlorinating agent is selected from the group consisting of POCl$_3$, POCl$_5$, and SOCl$_2$.

5. The process of claim 4, wherein said reducing step comprises contacting said 2-alkoxycarbonyl-3,5-dimethyl-4-alkoxypyridine with a reducing agent selected from the group consisting of LiAlH$_4$/NaBH$_4$/NaBH$_4$/Lewis acid, NaBH$_4$/tetrahydrofuran, NaBH$_4$/tetrahydrofuran/MeOH, AlH$_3$, and diisobutylaluminum hydride to obtain said 2-hydroxymethyl-3,5-dimethyl-4-methoxypyridine.

6. The process of claim 5, wherein said N-benzyl-2-alkoxycarbonyl-3,5-dimethyl-4-pyridone or said N-substituted benzyl-2-alkoxycarbonyl-3,5-dimethyl-4-pyridone is converted to said 2-alkoxycarbonyl-3,5-dimethyl-4(1H)-pyridone by hydrogenation.

7. The process of claim 3, wherein said reducing step comprises contacting said 2-alkoxycarbonyl-3,5-dimethyl-4-alkoxypyridine with a reducing agent selected from the group consisting of $LiAlH_4$, $NaBH_4$, $BH_3$/Lewis acid, $NaBH_4$/tetrahydrofuran, $NaBH_4$/tetrahydrofuran/MeOH, $AlH_3$, and diisobutylaluminum hydride to obtain said 2-hydroxymethyl-3,5-dimethyl-4-methoxypyridine.

8. The process of claim 7, wherein said N-benzyl-2-alkoxycarbonyl-3,5-dimethyl-4-pyridone or said N-substituted benzyl-2-alkoxycarbonyl-3,5-dimethyl-4-pyridone is converted to said 2-alkoxycarbonyl-3,5-dimethyl-4(1H)-pyridone by hydrogenation.

9. The process of claim 3, wherein said acylating step comprises contacting said 2-methyl-1-penten-1-alkoxy-3one with a dialkyloxylate to obtain said 2-alkoxycarbonyl-3,5-dimethyl-4-pyrone; the two alkyl groups of said dialkyloxylate being the same or different.

10. The process of claim 7, wherein said chlorinating agent is selected from the group consisting of $POCl_3$, $POCl_5$, and $SOCl_2$.

11. The process of claim 8, wherein said reducing step comprises contacting said 2-alkoxycarbonyl-3,5-dimethyl-4-alkoxypyridine with a reducing agent selected from the group consisting of $LiAlH_4$, $NaBH_4$, $BH_3$/Lewis acid, NaBH4/tetrahydrofuran, $NaBH_4$/tetrahydrofuran/MeOH, $AlH_3$, and diisobutylaluminum hydride to obtain said 2-hydroxymethyl-3,5-dimethyl-4-methoxypyridine.

12. The process of claim 11, wherein said N-benzyl-2-alkoxycarbonyl-3,5-dimethyl-4-pyridone or said N-substituted benzyl-2-alkoxycarbonyl-3,5-dimethyl-4-pyridone is converted to said 2-alkoxycarbonyl-3,5-dimethyl-4(1H)-pyridone by hydrogenation.

13. The process of claim 7, wherein said reducing step comprises contacting said 2-alkoxycarbonyl-3,5-dimethyl-4-alkoxypyridine with a reducing agent selected from the group consisting of $LiAlH_4$, $NaBH_4$, $BH_3$/Lewis acid, $NaBH_4$/tetrahydrofuran, $NaBH_4$/tetrahydrofuran/MeOH, $AlH_3$, and diisobutylaluminum hydride to obtain said 2-hydroxymethyl-3,5-dimethyl-4-methoxypyridine.

14. The process of claim 13, wherein said N-benzyl-2-alkoxycarbonyl-3,5-dimethyl-4-pyridone or said N-substituted benzyl-2-alkoxycarbonyl-3,5-dimethyl-4-pyridone is converted to said 2-alkoxycarbonyl-3,5-dimethyl-4(1H)-pyridone by hydrogenation.

15. The process of claim 3, wherein said ammonolyzing step comprises contacting said 2-alkoxycarbonyl-3,5-dimethyl-4-pyrone with benzylamine to obtain said N-benzyl-2-alkoxycarbonyl-3,5-dimethyl-4pyridone.

16. The process of claim 15, wherein said N-benzyl-2-alkoxycarbonyl-3,5-dimethyl-4-pyridone is converted to said 2-alkoxycarbonyl-3,5-dimethyl-4(1H)-pyridone by hydrogenation.

17. The process of claim 16, wherein said acylating step comprises contacting said 2-methyl-1-penten-1-alkoxy-3-one with diethyloxylate to obtain said 2-alkoxycarbonyl-3,5-dimethyl-4-pyrone.

18. The process of claim 17, wherein the alkoxy of said 2-methyl-1-penten-1-alkoxy-3-one is selected from the group consisting of ethoxy, propoxy, iso-propoxy, butoxy, and benzyloxy.

19. The process of claim 15, wherein said acylating step comprises contacting said 2-methyl-1-penten-1-alkoxy-3-one with diethyloxylate to obtain said 2-alkoxycarbonyl-3,5-dimethyl-4-pyrone.

20. The process of claim 15, wherein the alkoxy of said 2-methyl-1-penten-1-alkoxy-3-one is selected from the group consisting of ethoxy, propoxy, iso-propoxy, butoxy, and benzyloxy.

* * * * *